US012805939B2

(12) United States Patent
Nguyen et al.

(10) Patent No.: US 12,805,939 B2
(45) Date of Patent: Nov. 24, 2026

(54) METHOD AND SYSTEM FOR NAVIGATING A REAMER IN COMPUTER-ASSISTED SURGERY

(71) Applicant: ORTHOSOFT ULC, Montreal (CA)

(72) Inventors: Tin Nguyen, Laval (CA); Julie Deslongchamps, Brossard (CA); Jeremie Menard, Montréal (CA); Jerome Harrison, Montréal (CA); Fanny Batier, Montréal (CA); Yann Zimmermann, Montréal (CA)

(73) Assignee: ORTHOSOFT ULC, Montreal (CA)

( * ) Notice: Subject to any disclaimer, the term of this patent is extended or adjusted under 35 U.S.C. 154(b) by 166 days.

(21) Appl. No.: 18/955,019

(22) Filed: Nov. 21, 2024

(65) Prior Publication Data

US 2025/0160854 A1 May 22, 2025

Related U.S. Application Data

(60) Provisional application No. 63/601,886, filed on Nov. 22, 2023.

(51) Int. Cl.
*A61B 34/10* (2016.01)
*A61B 17/16* (2006.01)
*A61B 34/20* (2016.01)

(52) U.S. Cl.
CPC .......... *A61B 34/10* (2016.02); *A61B 17/1664* (2013.01); *A61B 17/1666* (2013.01); *A61B 34/20* (2016.02); *A61B 2034/107* (2016.02); *A61B 2034/2055* (2016.02); *A61B 2034/2065* (2016.02)

(58) Field of Classification Search
CPC . A61B 17/1664; A61B 17/1666; A61B 34/10; A61B 2034/107; A61B 34/20; A61B 2034/2055; A61B 2034/2065
See application file for complete search history.

(56) References Cited

U.S. PATENT DOCUMENTS 11,801,062 B2 * 10/2023 Nguyen ............ A61B 17/1659

* cited by examiner

*Primary Examiner* — Larry E Waggle, Jr.
(74) *Attorney, Agent, or Firm* — NORTON ROSE FULBRIGHT CANADA LLP

(57) ABSTRACT

A system including a registering device for registering a center of rotation of a hemispheric reamer in computer-assisted surgery may include: a hollow body defining an inner cavity having an open end configured for receiving a hemispheric reamer therethrough. The inner cavity has a frustoconical or conical abutment surface of a right circular cone having a central axis, the frustoconical or conical abutment surface configured for abuttingly receiving the hemispheric reamer therein. When the hemispheric reamer is at a closest point to an apex of the right circular cone while abuttingly received against the frustoconical or conical abutment surface, a center of rotation of the hemispheric reamer is on the central axis of the right circular cone, whereby a concurrent tracking of the registering device and of the hemispheric reamer sets the center of rotation for the hemispheric reamer.

13 Claims, 4 Drawing Sheets

METHOD AND SYSTEM FOR NAVIGATING A REAMER IN COMPUTER-ASSISTED SURGERY

CROSS-REFERENCE TO RELATED APPLICATION

The present application claims the priority of U.S. Patent Application No. 63/608,329, filed on Nov. 22, 2023 and incorporated herein by reference.

TECHNICAL FIELD

The present disclosure relates to computer-assisted surgery systems and, more particularly, to a method, system and/or a device for navigating a hemispheric reamer during computer-assisted surgery.

BACKGROUND

Navigation technologies are commonly used in computer-assisted surgery. Navigation technologies may involve the use of cameras or like imaging device that may track objects such as patient tissues and tools during a surgical procedure. The objects may consequently be tracked in a global referential system for the relative positions and orientations of the objects to be calculable in real time.

During hip surgery, the acetabulum of the pelvis may be reamed in preparation to an implanting of a cup. A hemispheric reamer, a.k.a., acetabular reamer, such as that shown in FIG. 1 may be used. The hemispheric reamer has a basket defining a hemispheric surface (i.e., including any truncated spherical surface) with teeth that grate the surface of the acetabulum while being driven in rotation. Reaming residue accumulates in the basket.

In order to navigate the acetabular reaming depth in three-dimensional space during surgery, the accuracy of the navigation may rely on the computer-assisted system knowing the diameter (or radius) of the reamer basket, but also the center of rotation since the operator may wish to know how deep to ream without fear thinning the acetabular bone wall too much. In some instances, while a reamer basket may be available in the form of manufacturer specifications, in practice there may be a difference between specification and actual physical diameter. Also, the specified diameter may be within a given range taking into account tolerances, such that the actual physical diameter may be unknown with precision. Moreover, if a reamer basket is reused, it may have reduced in diameter because of wear.

There are challenges to overcome when attempting to determine the center of rotation of the reamer basket, considering the different reamer basket designs, notably the shape, the manufacturing controls, the position of the connection relative to the center of rotation, the unknown diameter. In terms of reamer basket designs, there are numerous types of reamers, distinct for example because of the connection bar(s) they have, such as bridgeback, crossbar, flat crossbar, crossbar bump. Some reamer baskets do not have their connection right at the center of rotation or do not even control its position. For example, as observed from FIG. 1, the center of rotation may be offset from a trailing edge of the basket. The reamer baskets may also vary in shape if they were designed for minimally-invasive surgery or a standard exposure. Therefore, it poses a challenge to scope the entire spectrum of variability for acetabular reamers, and ensure that manufacturer specifications are accurate. Moreover, the reamers may be used and connected to different types of reaming devices (e.g., drill), which may also contribute to a lack of accuracy in determining the location of the center of rotation of the acetabular cup.

SUMMARY

In one aspect, there is provided a computer-assisted surgery system for tracking a hemispheric reamer, comprising: a registering device having a frustoconical or conical abutment surface of a right circular cone having a central axis, the frustoconical or conical abutment surface configured for abuttingly receiving a hemispheric reamer therein while on a reaming device; at least one processing unit; and a non-transitory computer-readable memory communicatively coupled to the processing unit and comprising computer-readable program instructions executable by the processing unit for: tracking a reaming device having a hemispheric reamer mounted to its shaft, concurrently tracking the registering device, registering a center of rotation of the hemispheric reamer relative to the tracking of the reaming device when the hemispheric reamer is at a closest point to an apex of the right circular cone while abuttingly received against the frustoconical or conical abutment surface of the registering device, and subsequently tracking the center of rotation of the hemispheric reamer while tracking the reamer device.

Further in accordance with the aspect, for instance, the hemispheric reamer is provided.

Still further in accordance with the aspect, for instance, a plurality of the hemispheric reamer are provided, wherein the plurality includes hemispheric reamers of different diameters, the registering device being usable with the plurality of the hemispheric reamer.

Still further in accordance with the aspect, for instance, the reaming device is provided.

Still further in accordance with the aspect, for instance, trackable members are on a support connected to the reaming device, the trackable members being optically trackable members.

Still further in accordance with the aspect, for instance, trackable members are on a support connected to the registering device, the trackable members being optically trackable members.

Still further in accordance with the aspect, for instance, the computer-readable program instructions are executable by the processing unit for calculating a diameter or radius of the hemispheric reamer using a depth of penetration of the hemispheric reamer in the registering device.

Still further in accordance with the aspect, for instance, the computer-readable program instructions are executable by the processing unit for outputting the diameter or the radius of the hemispheric reamer.

Still further in accordance with the aspect, for instance, the computer-readable program instructions are executable by the processing unit for outputting a discrepancy between the diameter or the radius of the hemispheric reamer, and specified dimensions of the hemispheric reamer.

Still further in accordance with the aspect, for instance, the computer-readable program instructions are executable by the processing unit for tracking a bone concurrently with the tracking of the center of rotation of the hemispheric reamer Still further in accordance with the aspect, for instance, the computer-readable program instructions are executable by the processing unit for outputting a depth of penetration of the hemispheric reamer in the bone using the concurrent tracking of the bone and tracking of the center of rotation, using the diameter or radius of the hemispheric reamer.

Still further in accordance with the aspect, for instance, the computer-readable program instructions are executable by the processing unit for tracking a bone concurrently with the tracking of the center of rotation of the hemispheric reamer Still further in accordance with the aspect, for instance, the computer-readable program instructions are executable by the processing unit for outputting a depth of penetration of the hemispheric reamer in the bone using the concurrent tracking of the bone and tracking of the center of rotation, using a diameter or radius of the hemispheric reamer.

In another aspect, there is provided a registering device for registering a center of rotation of a hemispheric reamer in computer-assisted surgery, comprising: a hollow body defining an inner cavity having an open end configured for receiving a hemispheric reamer therethrough, the inner cavity having a frustoconical or conical abutment surface of a right circular cone having a central axis, the frustoconical or conical abutment surface configured for abuttingly receiving the hemispheric reamer therein, wherein the registering device is trackable, and wherein, when the hemispheric reamer is at a closest point to an apex of the right circular cone while abuttingly received against the frustoconical or conical abutment surface, a center of rotation of the hemispheric reamer is on the central axis of the right circular cone, whereby a concurrent tracking of the registering device and of the hemispheric reamer sets the center of rotation for the hemispheric reamer.

In accordance with the other aspect, for example, trackable members are provided on a support, the trackable members being optically trackable members.

Still further in accordance with the other aspect, for instance, a kit may include: the registering device as described above and herein; and at least one hemispheric reamer.

Still further in accordance with the other aspect, for instance, the kit may include a plurality of the at least one hemispheric reamer, wherein the plurality includes hemispheric reamers of different diameters.

In another aspect, there is provided a computer-assisted surgery system for tracking a hemispheric reamer, comprising: at least one processing unit; a non-transitory computer-readable memory communicatively coupled to the processing unit and comprising computer-readable program instructions executable by the processing unit for: tracking a reaming device having a hemispheric reamer mounted to its shaft, concurrently tracking a registering device having a frustoconical or conical abutment surface of a right circular cone having a central axis, the frustoconical or conical abutment surface configured for abuttingly receiving the hemispheric reamer therein while on the reaming device, registering a center of rotation of the hemispheric reamer relative to the tracking of the reaming device when the hemispheric reamer is at a closest point to an apex of the right circular cone while abuttingly received against the frustoconical or conical abutment surface of the registering device, and subsequently tracking the center of rotation of the hemispheric reamer while tracking the reamer device.

DESCRIPTION OF THE DRAWINGS

Reference is now made to the accompanying figures in which.

DETAILED DESCRIPTION

Figure 1:
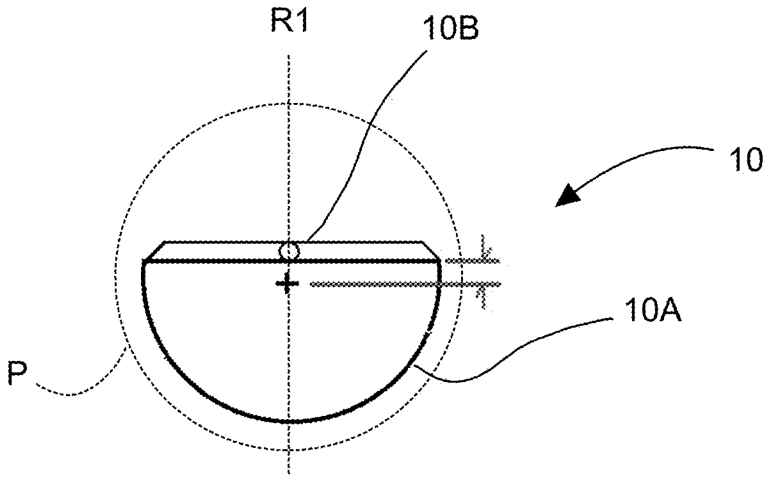
FIG. 1 (PRIOR ART)
FIG. 1 is a schematic view of a hemispheric reamer.
Figure 2:
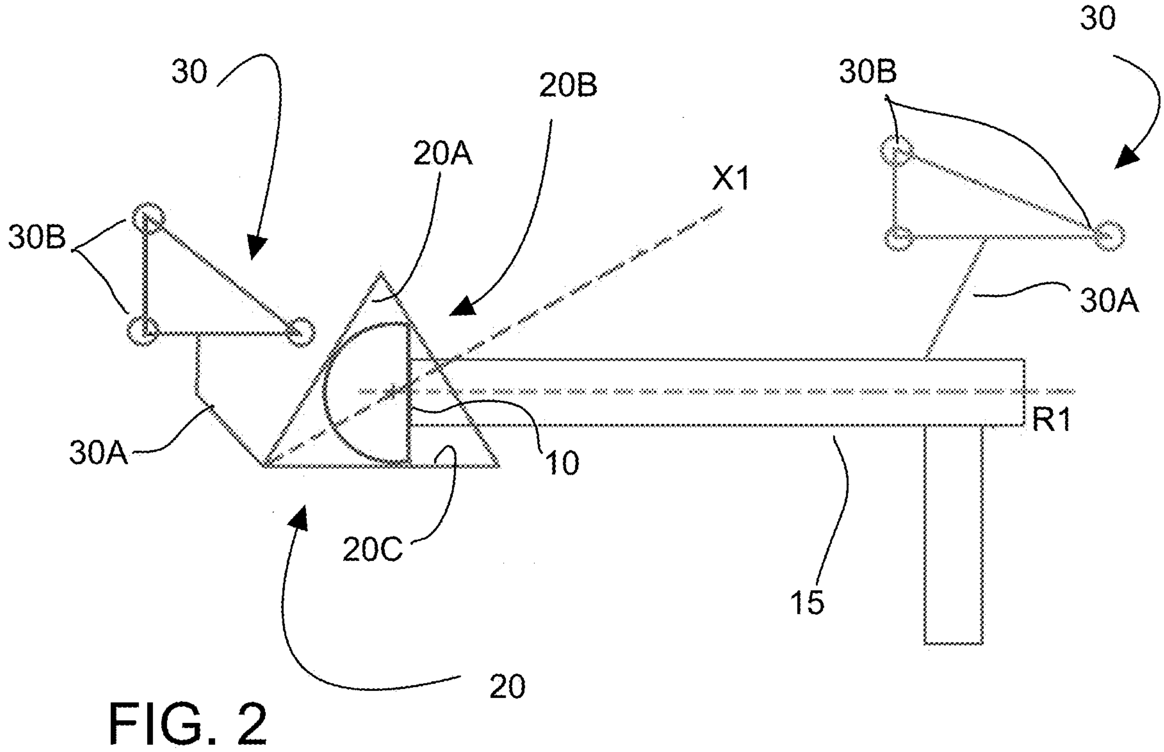
FIG. 2 is a schematic view of a hemispheric reamer on a reaming device, as coupled to a registering device of the present disclosure.
Figure 3:
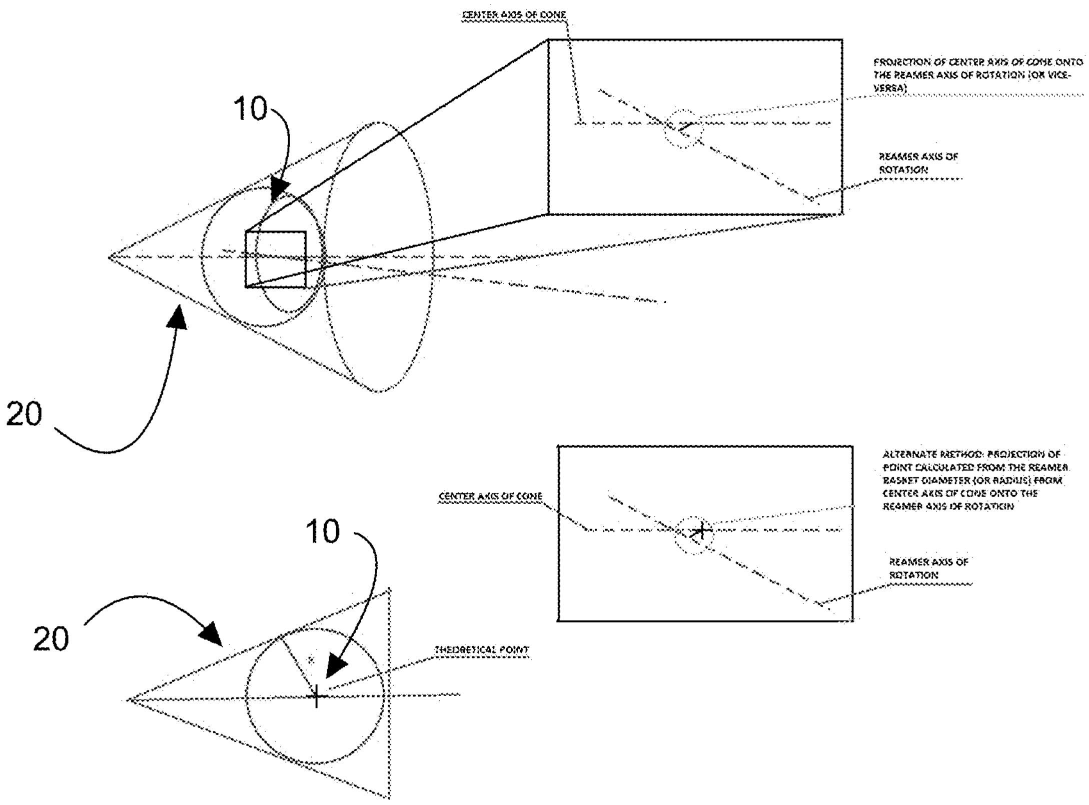
FIG. 3 is a schematic view of the hemispheric reamer coupled to the registering device as in FIG. 2, showing a correlation between axes.

Referring to the drawings and more particularly to FIGS. 1-3, a hemispheric reamer 10 is shown in combination with a reaming device 15 and a registering device 20. The reamer 10 is referred to herein as a hemispheric reamer, a.k.a., acetabular reamer. The hemispheric reamer 10 has a basket 10A defining a hemispheric surface. While the expression "hemispheric" is used herein, it is not used in a restrictive manner, namely it does not entail exactly half of a sphere. It therefore includes any truncated spherical surface used as a reamer. Although not shown discretely, the hemispheric reamer 10 has teeth with openings that operate concurrently to grate the surface of the acetabulum while being driven in rotation by the reaming device 15. Reaming residue accumulates in the basket 10A. The teeth are illustrated by way of the virtual reaming periphery P. The reaming periphery P is the spherical surface in which the radialmost tips or ends of the teeth of the basket 10A. The reaming periphery P is taken into consideration as the acetabulum is reamed to the shape of the reaming periphery P. A diameter or radius R of the reamer 10 may be that of the reaming periphery P. The reamer 10 may further include one or more crossbars 10B that serve as connector for the reamer 10 to be mounted to the reaming device 15. The crossbar 10B may be in accordance with any configuration, such as bridgeback, crossbar, flat crossbar, crossbar bump, to name but a few. The reamer 10 has a rotational axis R1 (a.k.a., central axis), and a center of rotation shown as +, that lies on the rotational axis R1.

The reaming device 15 is of the type that has a shaft that is driven in rotation. The rotational axis of the shaft may be collinear with the rotational axis R1 of the reamer 10. For example, the reaming device 15 may be referred to as a drill, a drilling tool, a drilling device. In FIG. 2, the reaming device 15 is shown as being of the hand-held type. However, the reamer 10 may be mounted to the end effector of a robot arm, such as an end effector featuring a shaft. Moreover, the reaming device 15 may be manipulated by a robot arm, in a computer-assisted robotized system, or supported by a robot arm with a user pulling the trigger of the reaming device 15.

The reaming device 15 (or robot arm supporting the reamer 10, etc) may be navigated during the surgical procedure, i.e., tracked for position and orientation during the surgical procedure. As the reamer 10 is in a fixed position on the shaft, a tracking of the reaming device 15 allows a tracking of features of the reamer 10, including the center of rotation.

Referring to FIG. 2, an exemplary tracker 30 is shown secured to the reaming device 15, and may also or alternatively be on the robot arm. The exemplary tracker 30 may be known as trackable elements, markers, navigation markers, active sensors (e.g., wired or wireless) that may for example include infrared emitters. In a variant, the tracker 30 includes a support 30A upon which are mounted passive retro-reflective elements 30B, that reflect light. The elements 30B are arranged in a known geometry (e.g., a scalene triangle) so as to be recognizably through detection by a tracker device 40 (FIG. 4), described in further detail below.

For example, the elements 30B may be retro-reflective tokens, patches, spheres, etc. In an example, the tracker 30 of FIGS. 2 and 4 may be as described in U.S. Pat. No. 8,386,022 and may thus be known as a multifaceted tracker. The tracker 30 may alternatively be made of passive elements, such as LEDs, that emit light or like signal.

While the tracker 30 is shown as being of optical nature, it is considered to use different tracking modalities as an alternative to the tracker 30 shown in FIG. 2. For example, it is contemplated to place a recognizable token, e.g., QR code, token, pattern or the like, on the reaming device 15. The tracking may then be performed by a camera unit, such as a 3D camera, that has suitable resolution to track the reaming device 15 and reamer 10 within the precision requirements of computer-assisted surgery. The 3D camera may also perform the tracking without such QR code or equivalent. The 3D camera may be used to generate a model of the reaming device 15, i.e., a virtual 3D model, which model is then tracked in position and orientation. As an alternative to a full 3D model, the 3D model may use prominent visual features of the reaming device 15 to track it.

The registering device 20 is shown in FIGS. 2 and 3. The expression "registering" is used because the device 20 is used to register, record, or set the center of rotation of the reamer 10. The registering device 20 may also be said to be universal, in that different sizes of reamer 10 may be used with the registering device 20.

The registering device 20 may have a hollow body defining an inner cavity 20A. The hollow body is shown having an open end 20B configured for receiving a hemispheric reamer 10 therethrough, for the hemispheric reamer 10 to enter the inner cavity 20A. The inner cavity 20A has an abutment surface 20C, that is part of a right circular cone having a central axis X1. The abutment surface 20C may be referred to as being conical, as the inner cavity 20A of the registering device 20 is shown as defining a full cone, up to an apex. However, the abutment surface 20C may be frustoconical, in that the inner cavity 20A may be a truncated cone, i.e., without a physical apex. The abutment surface 20C is configured for abuttingly receiving the hemispheric reamer 10 therein, in the manner shown in FIGS. 2 and 3. It may be said that it is the reaming periphery P of the reamer 10 that comes into contact with the abutment surface 20C, considering that the radialmost points of the basket 10A are the teeth.

Figure 4:
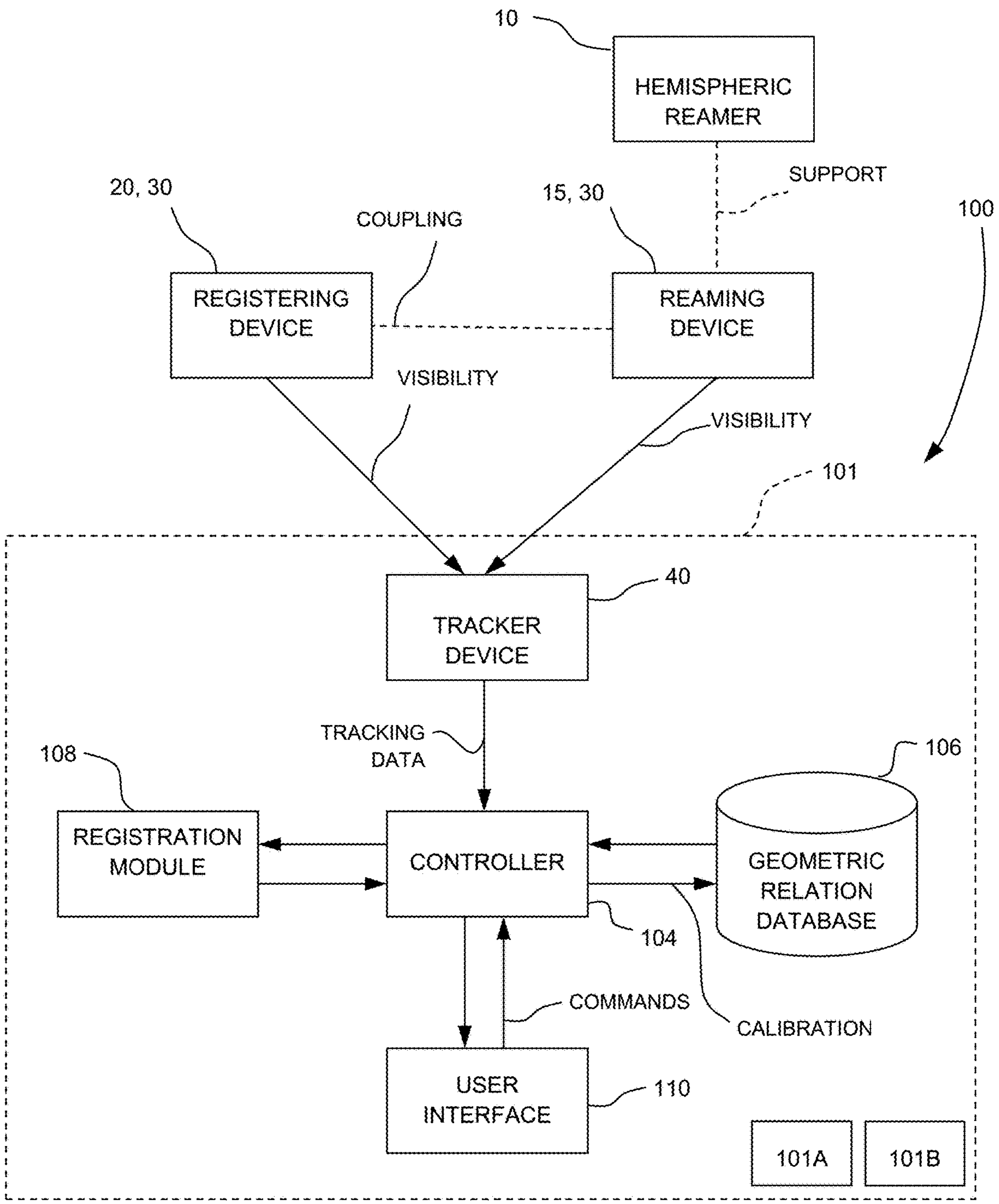
FIG. 4 is a diagram of a system for navigating a reamer in hip surgery in accordance with another embodiment of the present disclosure.

The outer surface of the hollow body is not limited to having a conical shape. It may for example have surface features, a handle, etc, to be supported or handled with ease. Moreover, the registering device 20 may also be provided with a tracker 30 that may be connected to the outer surface, or to any other part of the registering device 20 or to a support fixed to the registering device 20. The tracker 30 is shown as having a support 30A having trackable elements 30B. In a variant, the exemplary tracker 30 is of the same type as that on the reaming device 15 so as to be recognizable simultaneously through detection by the tracker device 40 (FIG. 4). The tracker 30 may thus be known as trackable elements, markers, navigation markers, active sensors (e.g., wired or wireless) that may for example include infrared emitters. In a variant, the tracker 30 includes a support 30A upon which are mounted passive retro-reflective elements 30B, that reflect light. The elements 30B are arranged in a known geometry, which geometry must differ from the geometry of the tracker 30 that is on the reaming device 15. Again, the elements 30B may be retro-reflective tokens, patches, spheres, active elements such as LEDs, etc. In an example, the tracker 30 on the registering device 20 of FIGS. 2 and 4 may be as described in U.S. Pat. No. 8,386,022 and may thus be known as a multifaceted tracker.

Again, while the tracker 30 on the registering device 20 is shown as being of optical nature, just like the tracker 30 on the reaming device 15, it is considered to use different tracking modalities as an alternative to the trackers 30 shown in FIG. 2. For example, it is contemplated to place a recognizable token, e.g., QR code, token, pattern or the like, on the registering device 20. The tracking may then be performed by a camera unit, such as a 3D camera, that has suitable resolution to track registering device 20 within the precision requirements of computer-assisted surgery. The 3D camera may also perform the tracking without such QR code or equivalent. The 3D camera may be used to generate a model of the reaming device 15, i.e., a virtual 3D model, which model is then tracked in position and orientation. As an alternative to a full 3D model, the 3D model may use prominent visual features of the registering device 20 to track it.

Therefore, the registering device 20 is trackable in space for position and orientation. Moreover, the geometrical relation between the registering device 20 and the tracker 30 (or other tracking modality) is known, such that a tracking of the registering device 20 via the tracking 30 or other tracking component or approach provides a tracking of the central axis X1, of the apex and of the abutment surface 21C.

In use, during the registration, the hemispheric reamer 10 is inserted in the inner cavity 20A of the device 20 via the open end 20B, so as to be at a closest point relative to the apex of the right circular cone (whether physical or imaginary), while being abuttingly received against the frustoconical or conical abutment surface 20C. Stated differently, the reamer 10 is moved as far as possible into the inner cavity 20A until blocked from moving further along toward the apex. Because of the spherical shape of the reamer 10, it may still be rotated, but the orientation of the reamer 10 relative to the device 20 is irrelevant to the registration procedure. This position including the closest point may be said to be a fully coupled position, a coupling arrangement, a mating arrangement. As explained below, in such coupled position, a center of rotation of the hemispheric reamer 10 is on the central axis X1 of the right circular cone of the device 20, such that the center of rotation may be set relative to the trackers 30. Also, if the radius R or diameter of the hemispheric reamer 10 is not known, it may be determined using the position of the center of rotation along the central axis X1 with respect to the apex of the right circular cone (i.e., depth of penetration). Subsequently, the tracking of the reamer 10 and of the reaming device 15, via the tracker 30, may include a position of the center of rotation, the radius R and the reaming periphery P. Moreover, the radius and/or diameter of the hemispheric reamer 10 may be displayed to inform the operator, such that the operator may be made aware of any discrepancy between specified reamer dimensions (i.e., manufacturer dimensions) and actual reamer dimensions.

By way of the registering device 20, the present disclosure pertains to a method that allows the determination of the center of rotation of any reamer basket used in a clinical setting while using a tracking system, such as the trackers 30 and the tracker device 40, or other tracking modality.

The proposed method uses a device such as the registering device 20 to calibrate the reamer 10 by registering the center of rotation of the reamer 10 for subsequent navigation. The registering device 20 has a cone shape to its inner cavity 20A (cone shape including frusto cone) that takes into account the different shapes and sizes of the reamer baskets 10A, with the conical geometry naturally allowing multiple contact points. The geometrical relation between the abutment surface 20C and the position and orientation of the tracker 30 is known (or can be set by calibration) and controlled. Thus, if the system tracks the tracker 30 on the registering device 20, the position and orientation of the abutment surface 20C is known in space. This may include the axis X1 of the right circular cone.

The reamer assembly including the reamer 10 mounted to the shaft of the reamer device 15 is fitted with another tracker 30, such that the geometrical relation between the axis of rotation R1 of the hemispheric reamer 10 and the tracker 30 is also known (or can be set by calibration) and controlled. The reamer basket 10A connected to the reaming device 15 is then introduced in the inner cavity 20A of the registering device 20, via the open end 20B. The basket 10A is advanced toward the apex of the registering device 20 as for as possible, i.e., closest to the apex within the inner cavity 20A, ensuring that there is proper peripheral contact. At this most advanced position of the basket 10A in the inner cavity 20A, the complementary geometries between a cone and a sphere are such that the center of the sphere (i.e., the center of rotation of the basket 10A) is precisely at the intersection of (1) the center axis X1 of the right circular cone defined by the registering device 20 (whether real as in FIG. 2 or imaginary for a truncated cone) with (2) the axis of rotation R1 of the reamer 10 as known. Therefore, in three dimensions, the method may include projecting one of the axes onto the other axis to locate the center of rotation. It may then be recorded relative to the tracker 30 of the reaming device 15, or other tracking modality (e.g., virtual model of the reaming device 15 for 3D camera).

As an alternative approach, as also shown in FIG. 3, if the value of the radius R of the reamer basket 10A is known, it can be used to determine the center of rotation as it can be projected onto the central axis X1 instead of calculating an intersection. However, such approach must rely on some certainty as to the radius R of the reamer basket 10, as the radius R may not be as specified due to wear, tolerances, etc, as explained above.

Thereafter, once the registration of the center of rotation of the reamer 10 has been set (i.e., recorded) relative to the reaming device 15, a tracking of the reaming device 15 may include continuous knowledge of the position of the center of rotation of the reamer 10. The information may be displayed in different possible values, including depth of penetration of the reamer 10 in a bone (e.g., by tracking the bone concurrently with the tracking of the reaming device 15, tracking of the reaming periphery P, etc.

Thus, the registering device 20 may be said to be a registering device for registering a center of rotation of a hemispheric reamer in computer-assisted surgery. The registering device 20 may have a hollow body defining an inner cavity having an open end configured for receiving a hemispheric reamer therethrough. The inner cavity may have a frustoconical or conical abutment surface of a right circular cone having a central axis, the frustoconical or conical abutment surface configured for abuttingly receiving the hemispheric reamer therein. The registering device is trackable such that, when the hemispheric reamer is at a closest point to an apex of the right circular cone while abuttingly received against the frustoconical or conical abutment surface, a center of rotation of the hemispheric reamer is on the central axis of the right circular cone, whereby a concurrent tracking of the registering device and of the hemispheric reamer sets the center of rotation for the hemispheric reamer.

Referring to FIG. 4, there is illustrated a computer-assisted surgery system 100 for navigating a reamer in hip surgery, that may be used for registering a center of rotation of a hemispheric reamer. The system 100 may be used and/or may include one or more of the reamers 10, such as reamers 10 of different sizes and configurations, the reaming device 15, and the registering device 20. Different tracking modalities may be used, and may be part of the system 100. This includes the trackers 30 of the optical type as shown in FIG. 2, as an example among others.

Still referring to FIG. 4, the computer-assisted surgery system 100 may be of the type used by surgeons or like operators manipulating tools, or by robotized surgery systems. For instance, the reaming device 15 may be part of a robot or manipulated by a robot arm. The computer-assisted surgery system 100 may incorporate the trackers 30 if present, as secured to the reaming device 15 and to the registering device 20 by way of a support or in any appropriate manner, such as those shown in FIG. 2, for example. The computer-assisted surgery system has a tracking system 101, which may be embodied by a computer having a processor 101A. A non-transitory computer-readable memory 101B may be communicatively coupled to the processing unit and comprising computer-readable program instructions executable, for instance in the form of a controller or a calculator module described below.

The tracking system 101 may include the tracker device 40 provided in order to visually track the trackers 30 if present. In FIG. 4, the tracker device 40 is shown as being embodied by an image capture device, capable of illuminating its environment, for compatibility with the trackers 30. In a variant, the tracker device 40 may have two (or more) points of view, such that triangulation can be used to determine the position of the tracker devices 30 in space, i.e., the coordinate system of the surgical procedure. The tracker device 40 may emit light, or use ambient light, to observe the trackers 30 from its points of view, so as to determine a position of the trackers 30 relative to itself. By knowing the geometry of the arrangements of trackers 30, the tracker device 40 can produce navigation data enabling the locating of objects within the coordinate system of the surgical procedure. In an embodiment, the tracker device 40 is of the type known as the Polaris products by Northern Digital Inc.

As per another embodiment, as discussed above in the embodiments without the trackable elements 30B, the tracker device 40 may be a stereoscopic camera, a 3D camera, a motion detection camera, etc. Thus, without trackers 30, the tracker device 40 may have the capacity to perform range imaging, and hence determine position data from the captured images during tracking. The expression 3D camera is used to describe the camera's capability of providing range data for the objects in the image or like footage it captures, but the 3D camera may or may not produce 3D renderings of the objects it captures. In contrast to structured light 3D imaging, range tracking does not seek specific illumination patterns in distance calculations, but relies instead on the images themselves and the 3D camera's capacity to determine the distance of points of objects in the images. Stated differently, the 3D camera for ranging performs non-structured light ranging, and the expression "ranging" is used herein to designate such non-structured light ranging. Such range tracking requires that the 3D camera be calibrated to achieve suitable precision and accuracy of tracking. In order to be calibrated, the tracking device 40 may use a known visual pattern in a calibration performed in situ, at the start of the tracking, and optionally updated punctually or continuously throughout the tracking.

The calibration is necessary to update the camera acquisition parameters due to possible lens distortion (e.g., radial, rotational distortion), and hence to rectify image distortion to ensure the range accuracy. Moreover, as described herein, tracking tokens with recognizable patterns may be used, with the patterns being used to determine a point of view (POV) of the tracking device 40, via perspective deformation.

A controller 104 is connected to the tracker device 40 Therefore, the controller 104 receives the tracking data from the tracker device 40. A database 106 may be provided so as to store the geometrical pattern data or other marks, such as optical patterns and/or geometrical information. More specifically, the geometrical relation between the reaming assembly of reaming device 15 with reamer 10 and its related tracker 30 (or model), and the geometrical relation between the registering device 20 and its related tracked 30 may be stored in the database 106. According to an embodiment, the geometrical pattern data includes a 3D virtual model of the registering device 20, including the abutment surface 20C. According to such an embodiment, the geometrical pattern data includes a 3D virtual model of the reaming device 15, including its rotational axis.

The geometrical relations may result from a calibration performed in the first steps of use of the computer-assisted surgery system, though the calibration may also be based on factory models, for example by the CAS system 100 retrieving a calibration file F for the tracker 30, the calibration file F having a geometry of the tracker 30 (e.g., length of the segments and angles of the scalene triangle in the example of FIG. 2). A calibration of the reaming device 15 with the tracker 30 thereon may be performed prior to the use of the tracker 30, to calibrate a rotational axis of the reaming device 15 relative to the tracker 30.

A registration module 108 is associated with the controller module 104. The registration module 108 receives the tracking from the tracker device 40, as well as the geometrical pattern data. Therefore, the registration module 108 distinguishes between the trackers 30 on the reaming device 15 and on the registering device 20. With the identification of the reaming device 15 and the registering device 20 being tracked, the registration module 108 may record the location of the center of rotation of the reamer 10 relative to the tracker 30 on the reaming device 15, along with related data. The registration module 108 is programmed to locate the center of rotation based on the complementarity between abutment surface 20C and reaming periphery P.

The position and orientation of the reamer 10, including the center of rotation, may be sent to the controller module 104. The controller module 104 may combine this information with the geometrical relations from the geometrical pattern database 106, so as to calculate the position of the center of rotation of the reamer 10 on the reaming device 15 and its tracker 30. From this point on, the controller 104 may calculate the position of the center of rotation of the reamer 10 relative to the tracker 30 on the reaming device 15, and outputs it as continuous tracking data, also referred to as navigation data. The system 100 may then track the reamer 10 with its center of rotation relative to a pelvis, if the pelvis in the coordinate system, such as by being tracked by another tracker 30. The radius and/or diameter of the hemispheric reamer 10 may be displayed on the user interface 110 to inform the operator, such that the operator may be made aware of any discrepancy between specific reamer dimensions and actual reamer dimensions. For example, the operator may be asked to confirm acceptance of the actual reamer dimensions before moving on to the reaming operation.

This information is sent to the user interface 110, such that the user of the computer-assisted surgery system obtains information pertaining to the position and orientation of the reamer 10, in the various forms known to computer-assisted surgery (e.g., visual representation, numerical values such as angles, distances, etc.). It is pointed out that the database 106 may as well be part of the controller module 104 or the registration module 108, may be part of a cloud-based server, etc.

Figure 5:
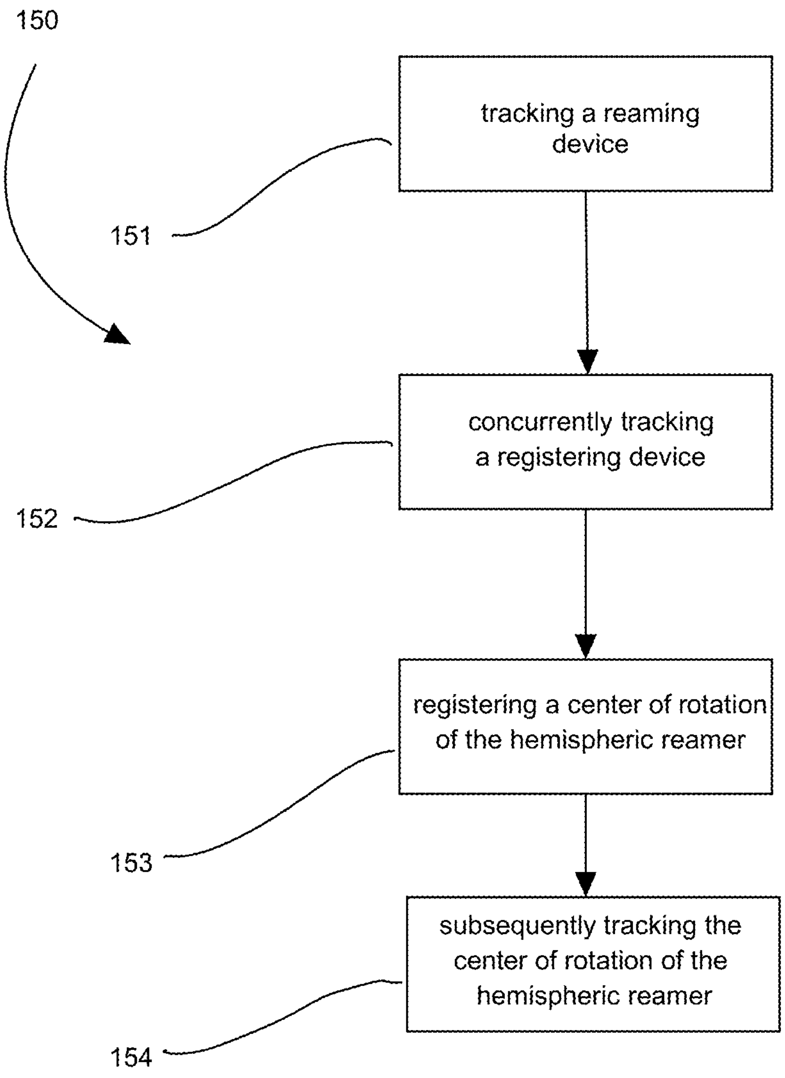
FIG. 5 is a flow chart of a method for navigation a hemispheric reamer in computer-assisted surgery.

Referring to FIG. 5, a method for navigating a reamer in computer-assisted surgery is generally shown as 150 and may include steps performed by a dedicated computer.

According to 151, a reaming device having a hemispheric reamer mounted to its shaft is tracked.

According to 152, a registering device having a frustoconical or conical abutment surface of a right circular cone having a central axis, the frustoconical or conical abutment surface configured for abuttingly receiving the hemispheric reamer therein while on the reaming device is tracked. The tracking at 151 and 152 may be concurrent.

According to 153, a center of rotation of the hemispheric reamer relative to the tracking of the reaming device is registered when the hemispheric reamer is at a closest point to an apex of the right circular cone while abuttingly received against the frustoconical or conical abutment surface of the registering device.

According to 154, the center of rotation of the hemispheric reamer is subsequently tracked while tracking the reamer device. This may include tracking the hemispheric reamer relative to the pelvis, such as during reaming of the acetabulum. The method may include outputting the center of rotation of the hemispheric reamer continuously, and in real time. Continuous tracking may include pauses.

The system 100 may also be referred to as a computer-assisted surgery system for tracking a hemispheric reamer, that may have at least one processing unit; a non-transitory computer-readable memory communicatively coupled to the processing unit and comprising computer-readable program instructions executable by the processing unit for: tracking a reaming device having a hemispheric reamer mounted to its shaft, concurrently tracking a registering device having a frustoconical or conical abutment surface of a right circular cone having a central axis, the frustoconical or conical abutment surface configured for abuttingly receiving the hemispheric reamer therein while on the reaming device, registering a center of rotation of the hemispheric reamer relative to the tracking of the reaming device when the hemispheric reamer is at a closest point to an apex of the right circular cone while abuttingly received against the frustoconical or conical abutment surface of the registering device, and subsequently tracking the center of rotation of the hemispheric reamer while tracking the reamer device.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. A computer-assisted surgery system for tracking a hemispheric reamer, comprising:

a registering device having a frustoconical or conical abutment surface of a right circular cone having a central axis, the frustoconical or conical abutment surface configured for abuttingly receiving a hemispheric reamer therein while on a reaming device;

at least one processing unit; and a non-transitory computer-readable memory communicatively coupled to the processing unit and comprising computer-readable program instructions executable by the processing unit for:

tracking a reaming device having a hemispheric reamer mounted to its shaft, concurrently tracking the registering device, registering a center of rotation of the hemispheric reamer relative to the tracking of the reaming device when the hemispheric reamer is at a closest point to an apex of the right circular cone while abuttingly received against the frustoconical or conical abutment surface of the registering device, and subsequently tracking the center of rotation of the hemispheric reamer while tracking the reamer device.

2. The system according to claim 1, including the hemispheric reamer.

3. The system according to claim 2, including a plurality of the hemispheric reamer, wherein the plurality includes hemispheric reamers of different diameters, the registering device being usable with the plurality of the hemispheric reamer.

4. The system according to claim 1, including the reaming device.

5. The system according to claim 4, including trackable members on a support connected to the reaming device, the trackable members being optically trackable members.

6. The system according to claim 1, including trackable members on a support connected to the registering device, the trackable members being optically trackable members.

7. The system according to claim 1, wherein the computer-readable program instructions are executable by the processing unit for calculating a diameter or radius of the hemispheric reamer using a depth of penetration of the hemispheric reamer in the registering device.

8. The system according to claim 7, wherein the computer-readable program instructions are executable by the processing unit for outputting the diameter or the radius of the hemispheric reamer.

9. The system according to claim 7, wherein the computer-readable program instructions are executable by the processing unit for outputting a discrepancy between the diameter or the radius of the hemispheric reamer, and specified dimensions of the hemispheric reamer.

10. The system according to claim 7, wherein the computer-readable program instructions are executable by the processing unit for tracking a bone concurrently with the tracking of the center of rotation of the hemispheric reamer.

11. The system according to claim 10, wherein the computer-readable program instructions are executable by the processing unit for outputting a depth of penetration of the hemispheric reamer in the bone using the concurrent tracking of the bone and tracking of the center of rotation, using the diameter or radius of the hemispheric reamer.

12. The system according to claim 1, wherein the computer-readable program instructions are executable by the processing unit for tracking a bone concurrently with the tracking of the center of rotation of the hemispheric reamer.

13. The system according to claim 12, wherein the computer-readable program instructions are executable by the processing unit for outputting a depth of penetration of the hemispheric reamer in the bone using the concurrent tracking of the bone and tracking of the center of rotation, using a diameter or radius of the hemispheric reamer.

* * * * *